(12) United States Patent
Doerr et al.

(10) Patent No.: US 8,019,415 B2
(45) Date of Patent: Sep. 13, 2011

(54) CARDIAC STIMULATOR WITH STIMULATION SUCCESS MONITORING

(75) Inventors: Thomas Doerr, Berlin (DE); Frank Tscherch, Bestensee (DE); Ulrich Tietze, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 443 days.

(21) Appl. No.: 12/403,266

(22) Filed: Mar. 12, 2009

(65) Prior Publication Data

US 2009/0264945 A1    Oct. 22, 2009

(30) Foreign Application Priority Data

Apr. 22, 2008   (DE) .......................... 10 2008 020 124

(51) Int. Cl.
*A61N 1/00* (2006.01)
(52) U.S. Cl. .......................................................... 607/4
(58) Field of Classification Search .................. 607/4
See application file for complete search history.

(56) References Cited

U.S. PATENT DOCUMENTS

| 5,193,550 A * | 3/1993 | Duffin | 600/510 |
| 7,941,208 B2 * | 5/2011 | Sauer et al. | 600/518 |
| 2004/0082975 A1 | 4/2004 | Meyer et al. | |
| 2006/0287681 A1 | 12/2006 | Yonce et al. | |
| 2006/0287685 A1 | 12/2006 | Meyer et al. | |
| 2007/0021793 A1 | 1/2007 | Voegele et al. | |
| 2007/0078489 A1 | 4/2007 | Meyer et al. | |
| 2008/0065161 A1 * | 3/2008 | Lian et al. | 607/4 |

OTHER PUBLICATIONS

German Search Report, dated Jan. 16, 2009.
European Search Report, dated Aug. 3, 2009.

* cited by examiner

*Primary Examiner* — George Manuel
(74) *Attorney, Agent, or Firm* — ARC IP Law, PC; Joseph J. Mayo

(57) ABSTRACT

An implantable cardiac stimulator having an at least partially electrically conductive housing, a ventricular stimulation unit connectable to left ventricular or right ventricular stimulation electrode and designed to generate ventricular stimulation pulses for stimulation of heart ventricle, having terminal for right ventricular defibrillation electrode. Has far-field electrogram detection unit (FFEDU) and stimulation success detecting unit (SSDU), of which FFEDU has first input connected to the terminal for right ventricular defibrillation electrode and second input connected to housing. FFEDU detects far-field electrocardiogram based on electric potentials applied to inputs and deliver these potentials to SSDU. SSDU has electrogram input and signal input receives a far-field electrogram generated by FFEDU and receives stimulation signal that represents a ventricular stimulation pulse generated and delivered by ventricular stimulation unit and analyzes section of received far-field electrogram immediately following delivery of ventricular stimulation impulse to determine whether it represents an effective or ineffective ventricular stimulation.

14 Claims, 3 Drawing Sheets

CARDIAC STIMULATOR WITH STIMULATION SUCCESS MONITORING

This application takes priority from German Patent Application DE 10 2008 124.3, filed 22 Apr. 2008, the specification of which is hereby incorporated herein by reference.

BACKGROUND OF THE INVENTION

1. Field of the Invention

The invention relates to a cardiac stimulator with stimulation success monitoring, i.e., a cardiac stimulator such as an implantable heart pacemaker or an implantable cardioverter/defibrillator (ICD), which is independently capable of detecting the efficacy of a stimulation pulse delivered to the heart.

2. Description of the Related Art

Cardiac stimulators of the aforementioned type are already known in particular as implantable heart pacemakers. In the implanted and functional state, such heart pacemakers are usually connected by an electrode line of the aforementioned type to an electrode implanted in the heart and are designed to deliver electric stimulation pulses to the heart, or more specifically to individual ventricles of the heart, via the electrode. The stimulation pulses serve to energize the cardiac tissue (myocardium) of the respective ventricle and are delivered in particular when the heart does not contract naturally at the proper time, depending on the type of heart pacemaker. A contraction is induced by an electric pulse delivered to the myocardium. If the electric pulse is strong enough, it has the effect of locally depolarized the myocardial tissue and causing it to contract accordingly. The depolarization and contraction of the myocardial tissue should expand over the entire stimulated myocardium and should thus lead to the desired contraction of the corresponding ventricle of the heart.

The corresponding electric stimulation pulse must have a stimulation intensity above a respective stimulus threshold of the myocardial tissue. The stimulus threshold is a measure of the minimum stimulation intensity sufficient to induce depolarization of the myocardium and thus induce contraction of the respective ventricle of the heart. The stimulus threshold depends on various factors and is also variable over a period of time under some circumstances. In addition to the requirement of delivering a stimulation pulse of a sufficient stimulation intensity, there is the need to keep the energy to be expended for a stimulation pulse as low as possible. This energy is usually obtained from a heart pacemaker battery, which becomes depleted over a period of time. When this battery is depleted, the implanted heart pacemaker must be replaced (in a surgical procedure) by a new heart pacemaker. The longest possible operating time of the heart pacemaker and thus the longest possible battery lifetime are thus desirable. Furthermore, the energy for a stimulation pulse should also be as low as possible but still sufficient to stimulate the myocardium alone but not the surrounding muscle tissue.

There is thus a need, firstly, for the stimulation intensity of a stimulation pulse to be sufficient to trigger a contraction of the myocardial tissue. A higher stimulation intensity is associated with a higher energy consumption with influencing variables that are otherwise unchanged. The stimulation intensity depends firstly on the duration of the stimulation pulse and secondly on the intensity of the stimulation pulse. The intensity of a stimulation pulse in turn depends on the electric voltage with which a stimulation pulse is delivered to the myocardial tissue. A higher stimulation intensity therefore regularly also leads to a higher energy consumption. To achieve more reliable stimulation of the myocardial tissue, stimulation pulses which, from an energy standpoint, consume slightly more energy than would be necessary at a minimum are often delivered.

On the other hand, there is a need to minimize the energy consumption per stimulation pulse because this energy is derived from a heart pacemaker battery, which thereby becomes depleted.

For this reason, there are known cardiac stimulators with stimulation success monitoring. The stimulation success may be monitored each time a stimulation pulse is delivered (beat-to-beat) in order to re-administer a stronger stimulus in the event a stimulus is ineffective (automatic capture control, ACC). Or the stimulation success may be monitored as part of an automatic stimulus threshold test (automatic threshold test, ATT), in which stimulation pulses of differing intensity are triggered in a controlled manner to thereby determine the intensity above which a stimulation pulse is effective and thereby determine the respective stimulation threshold.

In all cases, the most reliable possible detection of a stimulation success, i.e., stimulated contraction of the respective myocardial tissue, is important.

In this context, it is known that measurement of the stimulus threshold (detection of effective stimulation) is performed on the stimulation electrode, thereby resulting in measurement uncertainties due to polarization artifacts, autoshort artifacts and blanking artifacts.

Furthermore, not all types of electrodes are suitable for this method, so the known method cannot be used to an unlimited extent.

BRIEF SUMMARY OF THE INVENTION

The object of the invention is therefore
to allow measurement of the stimulus threshold when using any types of electrodes and
to ensure a high measure of reliability.

According to the invention, the solution to this problem utilizes an implantable cardiac stimulator, comprising
at least one defibrillation electrode (shock electrode) in the right ventricle (RV coil) and a sensing electrode for the right or left ventricle,
at least one pace/sense channel in the right or left ventricle,
a far-field channel derived from the shock electrode against the housing of the implant (hereinafter referred to as HV-ECG),
an analyzer unit for evaluating the HV-ECG immediately after delivery of a ventricular stimulation, which assesses the stimulus delivered previously as being effective or ineffective as a function of the analysis of the HV-ECG.

Depending on the assessment, the cardiac stimulator may then control its further behavior and may trigger, for example, the delivery of an efficient stimulation pulse after inefficient stimulation and, in the absence of intrinsic conduction, increase the pulse intensity when there is inefficient stimulation and/or retain or reduce the pulse intensity when there is effective stimulation.

The cardiac stimulator therefore has
an at least partially electrically conductive housing,
a ventricular stimulation unit which is connected or is designed to be connected to a left ventricular or right ventricular stimulation electrode, to generate and deliver ventricular stimulation pulses for stimulation of a ventricle of the heart, and
a terminal for a right ventricular defibrillation electrode.

Furthermore, the implantable cardiac stimulator has a far-field electrogram detection unit and a stimulation success detecting unit, of which the far-field electrogram detection unit has a first input which is connected to the terminal for the right ventricular defibrillation electrode and a second input connected to the electrically conductive housing. The far-field electrogram detection unit is designed to determine a far-field electrocardiogram on the basis of the electric potentials applied to the two inputs during operation and to output it to the stimulation success detecting unit. The stimulation success detecting unit has an electrogram input and a signal input and is designed to receive a far-field electrogram generated by the far-field electrogram detection unit via the electrogram input and to receive via the signal input a stimulation signal indicating a ventricular stimulation pulse generated and delivered by the ventricular stimulation unit, and to analyze a section of a received far-field electrogram which directly follows in time the delivery of a ventricular stimulation pulse, to determine whether it represents an effective or ineffective ventricular stimulation.

The following embodiment variants of the stimulation success detecting unit are preferred with regard to the assessment of the stimulation success by the stimulation success detecting unit:

the assessment of the stimulation success is based on the analysis of the interval in time between a stimulation pulse and the stimulation of the ventricle recorded in the far-field electrogram, the assessment of the stimulation success is based on the analysis of the dominant signal polarity of the stimulation of the ventricle recorded in the far-field electrogram, assessment of the stimulation success is based on the analysis of the interval in time between a stimulation pulse and the stimulation of the ventricle recorded in the far-field electrogram plus its dominant signal polarity, the assessment of the stimulation success is based on the comparison of a set of parameters determined from the far-field electrogram following the stimulation with a set of model parameters representing either capture or non-capture. Two sets of model parameters may also be available so that the stimulation success detecting unit may perform a type of cross-check by double comparison.

According to another preferred embodiment variant of the cardiac stimulator, the measured stimulus threshold is stored as diagnostic information and is transferred to an external device via home monitoring. To do so, the cardiac stimulator has a corresponding memory and a telemetry unit.

In the sense of the variants described previously, the cardiac stimulator (or more precisely its stimulation control unit) may be designed to perform an automatic adjustment of the stimulation energy in the sense of an automatic threshold test (ATT) for a period until the next test, i.e., not beat-to-beat, on the basis of the measured stimulus threshold.

Alternatively, the cardiac stimulator and/or its stimulation control unit may be designed to perform a beat-to-beat adjustment of the stimulation pulse intensity in the sense of an automatic capture control (ACC) based on the measured stimulus threshold. It is advantageous here if the cardiac stimulator is designed to trigger the most effective possible stimulus in the case when the stimulus is below the stimulus threshold (i.e., when lack of stimulation success is detected).

BRIEF DESCRIPTION OF THE DRAWINGS

The invention will now be explained in greater detail on the basis of an exemplary embodiment with reference to the figures, in which.

DETAILED DESCRIPTION OF THE INVENTION

Figure 1:
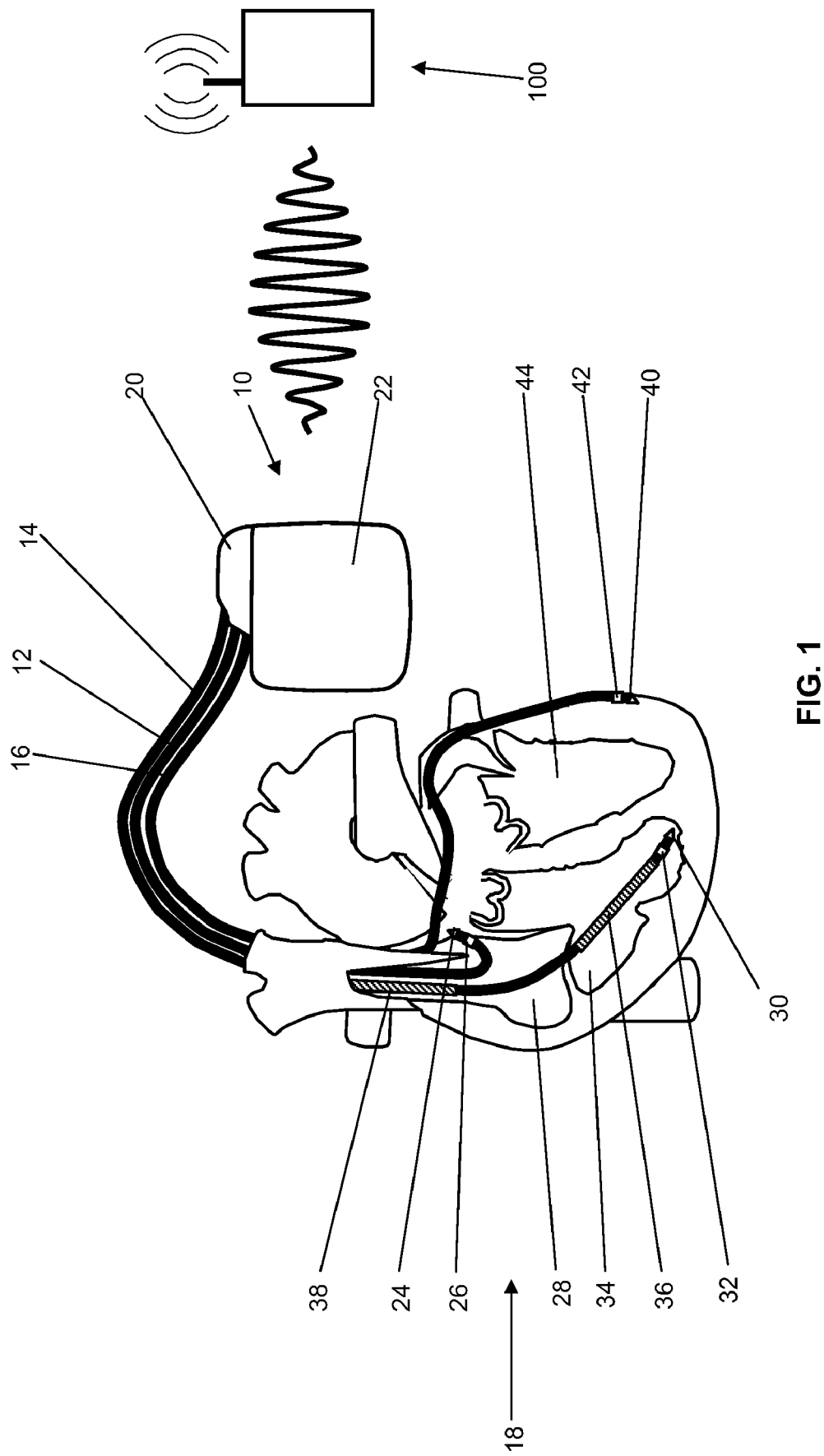
FIG. 1: shows an implantable triple-chamber cardiac stimulator with three electrodes to the patient's heart.

FIG. 1 shows an implantable cardiac stimulator 10 in the form of a triple-chamber heart pacemaker/cardioverter/defibrillator with electrode lines 12, 14, 16 connected to it and also connected to a heart 18. Furthermore, an external device 100 in the vicinity of the implantable cardiac stimulator 10 is also shown. The electrode lines 12, 14 and 16 are electrically connected via known standardized plug connections to contact bushings in a header (adapter housing) 20 of the cardiac stimulator 10. In this way, the electrode lines 12, 14 and 16 are also connected to electronic components in the interior of a hermetically sealed metal housing 22 of the cardiac stimulator 10. These components are presented schematically in greater detail below and determine the inventive functioning of the cardiac stimulator 10.

The electrode line 12 is a right atrial electrode line having an atrial tip electrode RA tip 24 on its distal end as well as, at a short distance therefrom, an atrial ring electrode or a ring 26, both of which are placed in the right atrium 28 of the heart 18.

The electrode line 14 is a right ventricular electrode line and has on its distal end a right ventricular tip electrode RV tip 30 and in the immediate proximity a right ventricular ring electrode RV ring 32. Both electrodes are arranged in the apex of the right ventricle 34 of the heart 18.

Furthermore, the right ventricular electrode line 14 also carries a right ventricular shock coil RV shock 36 as a large-area electrode for delivering defibrillation shocks. Another shock coil 38 is arranged in the superior vena cava and therefore is also referred to below as the SVC shock electrode.

Figure 2:
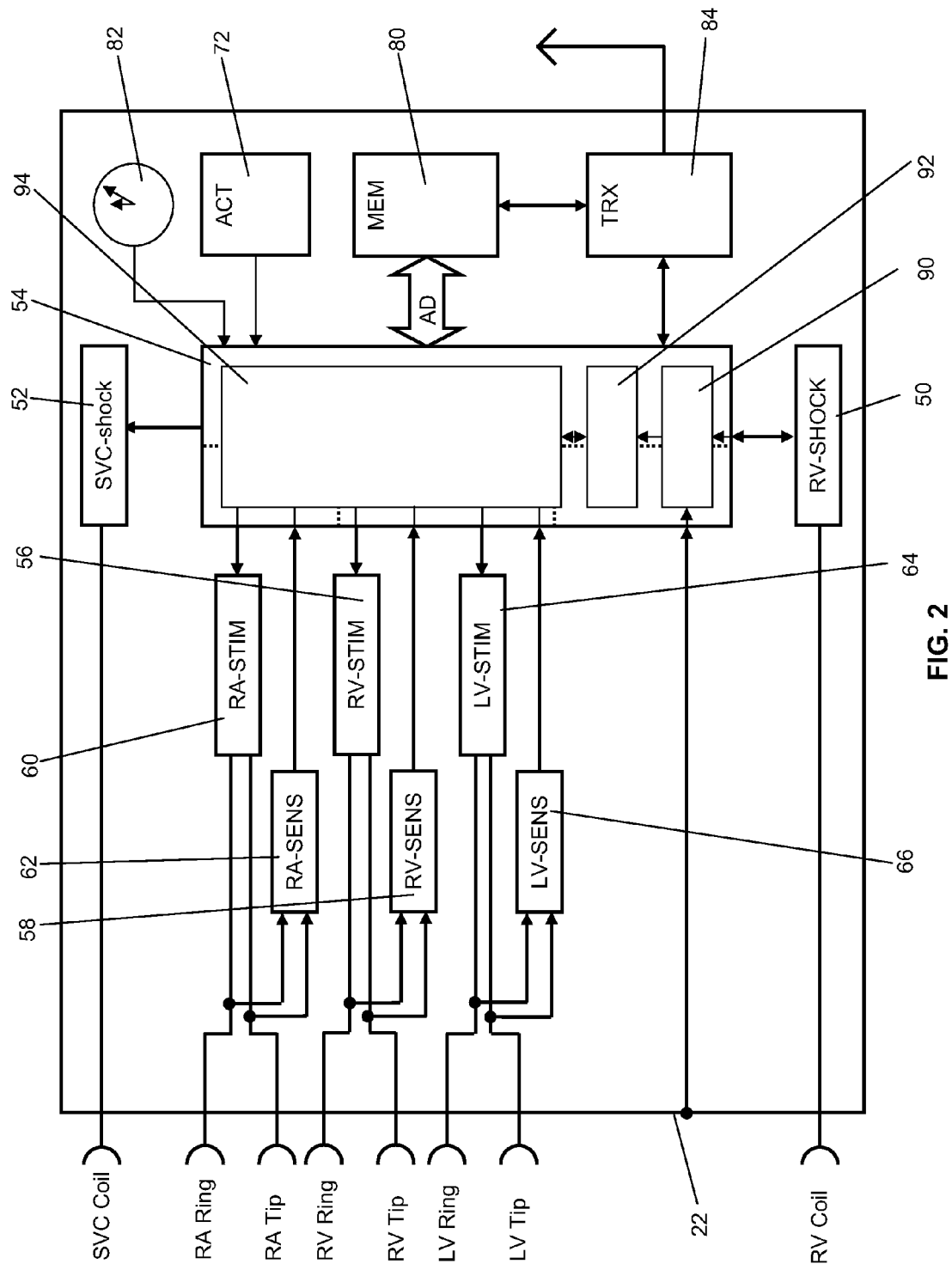
FIG. 2: shows a block diagram for implementation of the stimulus threshold measurement function.

The electrode line 16 is a left ventricular electrode line on whose distal end is arranged a left ventricular tip electrode LV tip 40 and in proximity of which is arranged a left ventricular ring electrode LV ring 42. Furthermore, the left ventricular electrode line 16 has a left ventricular shock coil which is not identified further here but is shown in FIG. 2 for delivering defibrillation shocks to the left ventricle 44. The left ventricular electrode line 16 is guided from the right atrium 28 of the heart 18 through the coronary sinus into a lateral vein branching off from the former and therefore is also referred to as the coronary sinus electrode line or CS electrode line.

The housing 22 of the cardiac stimulator 10 is at least partially conductive and itself forms a large-area electrode for receiving far-field potentials of the myocardium.

FIG. 2 shows the main components of the cardiac stimulator 10. On the left side are shown the electric terminals for the various electrodes 24, 26, 30, 32, 36, 38, 40 and 42. The shock electrodes 36 and 38 are both connected to a right ventricular shock pulse generator 50 and/or SVC shock generator 52. The two shock generators 50 and 52 are connected to a stimulation control unit 54 which controls the two shock pulse generators 50 and 52 as needed to generate and deliver a defibrillation shock.

The terminal for the right ventricular tip electrode RV tip and the terminal for the right ventricular ring electrode RV ring are both connected to a right ventricular stimulation unit 56 as well as to a right ventricular sensing unit 58. The right ventricular stimulation unit 56 as well as the right ventricular sensing unit 58 are both connected to the stimulation control unit 54.

The right ventricular stimulation unit 56 is designed to generate a right ventricular stimulation pulse in response to a trigger signal of the stimulation control unit 54 and to deliver the pulse to the right ventricular tip electrode RV tip in the connection to the right ventricular ring electrode RV ring. Alternatively, it is also possible for the housing 22 of the cardiac stimulator 10 to form a neutral electrode and for the right ventricular stimulation unit 56 to be connected to the terminal for the right ventricular ring electrode RV tip and to the housing 22 as another electrode for delivering a stimulation pulse. A right ventricular stimulation pulse differs from a defibrillation shock in that the stimulation pulse has a much lower pulse intensity, so it does not stimulate all of the myocardial tissue (myocardium) of a ventricle all at once in response to a beat like a defibrillation shock, but instead stimulates only the myocardial cells in the immediate vicinity of the right ventricular tip electrode RV tip 30. This stimulation then propagates through natural stimulus conduction over the entire right ventricle 34, thereby ensuring a stimulated contraction of the right ventricle 34.

The right ventricular sensing unit 58 is designed to amplify and filter electric potentials applied at the terminal for the right ventricular ring electrode RV ring and the right ventricular tip electrode RV tip first through an input amplifier and then to filter them. In addition, the right ventricular sensing unit 58 is designed to analyze the characteristic of the electric signals applied at its input such that the right ventricular sensing unit 58 automatically detects a natural (intrinsic), i.e., automatic contraction of the right ventricle 34. This may be accomplished, for example, by comparing the characteristic of the signal applied to the inputs of the right ventricular sensing unit 58 with a threshold value. Typically the greatest amplitude of the signal in the form of the so-called R wave is characteristic of a natural contraction of the right ventricle 34, which can be detected by comparison with a threshold value. The right ventricular sensing unit 58 then delivers a suitable output signal indicating a natural contraction of the right ventricle 34 to the stimulation control unit 54.

Similarly, the terminal for the right atrial tip electrode RA tip and the terminal for the right atrial ring electrode RA ring are connected to both a right atrial stimulation unit 60 and a right atrial sensing unit 62, which are in turn connected to the stimulation control unit 54. The right atrial stimulation unit 60 is designed to generate stimulation pulses, the intensity of which is sufficient to stimulate the right atrial myocardium. The right atrial stimulation pulses may have a different pulse intensity than the right ventricular stimulation pulses. The right atrial sensing unit 62 is designed to detect a so-called P wave from the characteristic of the differential signal applied at its inputs, said P wave characterizing a natural (intrinsic) contraction of the right atrium 28. If the right atrial sensing unit 62 detects a corresponding P wave, it generates an output signal and delivers this signal to the stimulation control unit 54, said signal characterizing a natural contraction of the right atrium 28.

Similarly, the terminal for the left ventricular tip electrode LV tip and the terminal for the left ventricular ring electrode LV ring are also connected to a left ventricular stimulation unit 64 and a left ventricular sensing unit 66. The left ventricular stimulation unit 64 and the left ventricular sensing unit 66 are likewise connected to the stimulation control unit 54. Both function like the stimulation units 56 and 60 and the sensing units 58 and 62 described above.

The cardiac stimulator 10 is capable of detecting ECG signals from all probes. In the case of the right ventricular electrode line 14, which forms an RV shock probe together with its right ventricular defibrillation electrode (shock coil 36, RV coil), the ECGs are derived from the terminal RV coil against the housing 22 of the implant and thus form a far-field signal (HV-ECG). The two leads of the atrial probe formed by the right atrial electrode line 12 and the LV probe formed by the left ventricular electrode line 16 are bipolar leads and form the near field signal. The right ventricular electrode line need not necessarily have a stimulation/sensing device for the present invention, i.e., the right ventricular tip electrode RV tip 30 and the right ventricular ring electrode RV ring 32 as well as the shock coil 38 in the superior vena cava may also be omitted in alternative embodiment variants of the invention.

The control unit 54 has a far-field electrogram detection unit 90, which is connected at one end to the housing 22 of the cardiac stimulator 10 and at the other end to the RV coil terminal for the right ventricular defibrillation electrode 36. The far-field electrogram detection unit 90 is designed to determine a far-field electrocardiogram on the basis of the electric potentials applied to the two inputs during operation. It has an output, which is connected to an electrogram input of a stimulation success detecting unit 92 and serves to transmit the respective far-field electrocardiogram to the stimulation success detecting unit 92. The stimulation success detecting unit 92 also has a signal input, which is connected to a stimulation control unit 94 of the control unit 54 and by which the stimulation success detecting unit 92 receives signals which indicate a ventricular stimulation pulse generated and delivered by the ventricular stimulation unit.

The stimulation success detecting unit 92 is designed to analyze a section of a received far-field electrogram following immediately on delivery of a ventricular stimulation pulse to determine whether it represents an effective or ineffective ventricular stimulation.

The stimulation control unit 94 is connected to the right ventricular stimulation unit 56 and the left ventricular stimulation unit and is designed to trigger them on demand for generating and delivering stimulation pulses with a set intensity. In addition, the stimulation control unit 94 is capable of setting the intensity of the stimulation pulses as a function of the respective stimulation success, as determined by the stimulation success detecting unit and to adjust, if necessary, the stimulation pulse intensity by setting the duration and/or the intensity (amplitude) of a stimulation pulse.

Of the elements illustrated in the block diagram in FIG. 2, the following contribute toward implementation of a measurement function for the left ventricular stimulation in the sense of the invention. The right atrial stimulation unit and the right atrial sensing unit form a right atrial channel and serve to synchronize the delivery of left ventricular stimulation pulses with the atrial activity of the patient. However, an embodiment without this atrial channel is also possible in principle. The left ventricular stimulation unit allows the delivery of pacemaker pulses to the left ventricle via a left ventricular electrode line 16 installed through the coronary sinus. The pulse parameters such as stimulation amplitude and pulse period are predefined here by the stimulation unit.

The ECG signal, which is derived by the right ventricular electrode line against the housing of the implant, is amplified by an ECG amplifier block as part of the far-field electrogram detection unit 90 and is filtered through a broadband filter in a suitable manner. The electrogram signal thereby obtained is evaluated by the stimulation control unit and a decision is made as to whether or not a stimulus delivered via the left ventricular electrode line 16 was efficient.

Figure 3:
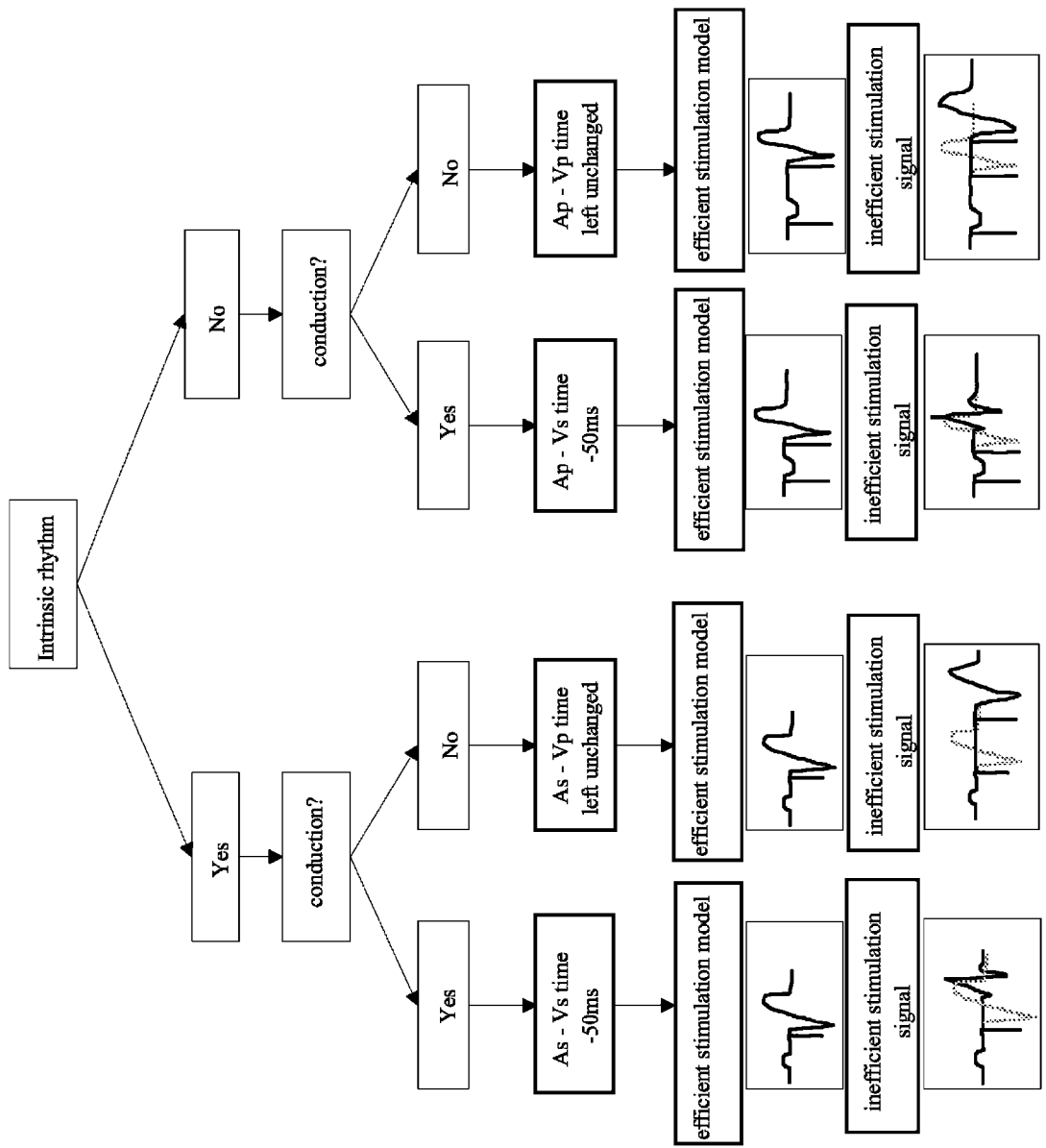
FIG. 3: shows an algorithm for determining the efficiency of ventricular stimulation.

On the basis of FIG. 3, a possible sequence for determining the efficiency of ventricular stimulation is explained. In principle, it does not play a role whether a stimulation pulse is delivered in the right or left ventricle. First, the prevailing rhythm and/or stimulation mode is determined. At an intrinsic sinus rhythm, the atrial stimulation pulses of the cardiac stimulator are suppressed, whereas if there is no sinus rhythm, atrial stimulation is performed.

If there is no AV block, the ventricle is not stimulated; if there is an AV block, the ventricle is stimulated. According to the mode found, a model of the prevailing far-field electrocardiogram is recorded with reliable ventricular stimulation. Next the efficiency can be checked by the simplest possible comparison with the model determined previously for each subsequent ventricular stimulation. If stimulation is inefficient, there is either a complete failure of ventricular stimulation or a shift in time. If a complete failure is found (when there is an AV block), there is a stimulation with a reliable amplitude and an AV time prolonged accordingly.

What is claimed is:

1. An implantable cardiac stimulator (10) comprising:
    an at least partially electrically conductive housing (22);
    a ventricular stimulation unit (56; 64) which is connected or connectable to a left ventricular stimulation electrode or a right ventricular stimulation electrode and is configured to generate and deliver ventricular stimulation pulses for stimulation of a ventricle of a heart;
    a terminal for a right ventricular defibrillation electrode (36);
    a far-field electrogram detection unit (90);
    a stimulation success detecting unit (92);
    wherein the far-field electrogram detection unit (90) has a first input that is connected to the terminal for the right ventricular defibrillation electrode and a second input that is connected to the at least partially electrically conductive housing, and wherein the far-field electrogram detection unit (90)
        is configured to detect a far-field electrogram based on electric potentials applied to the first and second inputs and to output the far-field electrogram to the stimulation success detecting unit (92); and,
    wherein the stimulation success detecting unit (92) has an electrogram input and a signal input and wherein the stimulation success detecting unit (92)
        is configured to receive the far-field electrogram generated by the far-field electrogram detection unit (90) via the electrogram input and to receive via the signal input a stimulation signal that indicates a ventricular stimulation pulse generated and delivered by the ventricular stimulation unit (56, 64) and
        is also configured to analyze a section of a received far-field electrogram that follows immediately in time after delivery of the ventricular stimulation pulse to determine whether it represents effective or ineffective ventricular stimulation.

2. The implantable cardiac stimulator according to claim 1, wherein the ventricular stimulation unit is a right ventricular stimulation unit (56).

3. The implantable cardiac stimulator according to claim 1, wherein the ventricular stimulation unit is a left ventricular stimulation unit (64).

4. The implantable cardiac stimulator according to claim 1, wherein the implantable cardiac stimulator further comprises a stimulation control unit (94) which is connected to a control output of the stimulation success detecting unit (92) and is configured to control delivery of the ventricular stimulation pulses as a function of whether an analyzed section of the received far-field electrogram represents said effective or ineffective ventricular stimulation.

5. The implantable cardiac stimulator according to claim 1, wherein the stimulation success detecting unit (92) is configured to perform an assessment of stimulation success through analysis of an interval in time between a point in time of delivery of a stimulation pulse and ventricular stimulation recorded in the far-field electrogram.

6. The implantable cardiac stimulator according to claim 1, wherein the stimulation success detecting unit (92) is configured to perform an assessment of stimulation success through analysis of a dominant signal polarity of ventricular stimulation recorded in the far-field electrogram.

7. The implantable cardiac stimulator according to claim 1, wherein the stimulation success detecting unit (92) is configured to perform an assessment of stimulation success through analysis of an interval of time between a point in time of delivery of a stimulation pulse and ventricular stimulation recorded in the far-field electrogram and through analysis of a dominant signal polarity.

8. The implantable cardiac stimulator according to claim 1, wherein the stimulation success detecting unit (92) is configured to perform an assessment of stimulation success through comparison of a set of parameters determined from the far-field electrogram that follows stimulation with respect to a model parameter set.

9. The implantable cardiac stimulator according to claim 8, wherein the model parameter set represents said stimulation success that represents a capture.

10. The implantable cardiac stimulator according to claim 8, wherein the model parameter set represents an inadequate stimulation success that represents a non-capture.

11. The implantable cardiac stimulator according to claim 1, wherein the implantable cardiac stimulator (10) further comprises:
    a memory (80);
    a telemetry unit (84); and,
    wherein the implantable cardiac stimulator is configured to store a measured stimulus threshold as diagnostic information and to transmit the diagnostic information wirelessly to the telemetry unit (84).

12. The implantable cardiac stimulator according to claim 1, wherein the implantable cardiac stimulator (10) is configured to perform an automatic adjustment of stimulation pulse intensity based on a measured stimulus threshold, that is ATT and not beat-to-beat.

13. The implantable cardiac stimulator according to claim 1, wherein the implantable cardiac stimulator (10) is configured to perform a pulse-to-pulse, that is a beat-to-beat adjustment of stimulation energy based on a measured stimulus threshold, that is ACC.

14. The implantable cardiac stimulator according to claim 13, wherein the implantable cardiac stimulator (10) is configured to deliver a stimulation pulse of a high intensity immediately in an event of an inadequate stimulation success.

* * * * *